United States Patent [19]

Luman et al.

[11] Patent Number: 5,403,320
[45] Date of Patent: Apr. 4, 1995

[54] BONE MILLING GUIDE APPARATUS AND METHOD

[75] Inventors: David P. Luman, Logan; Daniel A. Perkins, Roy, both of Utah

[73] Assignee: Venus Corporation, Ogden, Utah

[21] Appl. No.: 1,156

[22] Filed: Jan. 7, 1993

[51] Int. Cl.$^6$ ............................................. A61B 17/00
[52] U.S. Cl. ........................................ 606/89; 606/87; 606/79; 606/53
[58] Field of Search ................ 606/53, 79, 80, 84, 606/85, 86, 87, 89, 95

[56] References Cited

U.S. PATENT DOCUMENTS

| | | | |
|---|---|---|---|
| 4,399,813 | 8/1983 | Barber | 606/96 |
| 4,467,801 | 8/1984 | Whiteside | 606/88 |
| 4,738,256 | 4/1988 | Freeman et al. | 606/87 |
| 4,777,942 | 10/1988 | Frey et al. | 606/80 |
| 5,041,117 | 8/1991 | Engelhardt | 606/86 |
| 5,047,033 | 9/1991 | Fallin | 606/87 |
| 5,047,034 | 9/1991 | Sohngen | 606/87 |
| 5,129,909 | 7/1992 | Sutherland | 606/86 |
| 5,169,401 | 12/1992 | Lester et al. | 606/79 |
| 5,211,645 | 5/1993 | Baumgart et al. | 606/86 |

*Primary Examiner*—Stephen C. Pellegrino
*Assistant Examiner*—Jeffrey A. Schmidt
*Attorney, Agent, or Firm*—J. Winslow Young

[57] ABSTRACT

A bone milling guide apparatus and method for preparing the proximal end of a femur to receive a hip stem prosthesis in snug-fitting relationship. The ball portion of the femur is removed using conventional surgical techniques to expose the underlying cancellous bone. An axial bore is drilled in the intramedullary canal to receive the distal portion of the hip stem prosthesis. The proximal end of the axial bore is reamed to form a tapered recess which is dimensionally configured to receive a portion of the external surface of the proximal end of the hip stem prosthesis. A tapered, hollow body is inserted into the tapered recess and supports a U-shaped template extending outwardly therefrom. Each arm of the U-shaped template is affixed to the tapered, hollow body on each side of a longitudinal slot in the side of the tapered, hollow body. A bone miller is inserted coaxially into the hollow body and tilted angularly through the longitudinal slot to remove cancellous bone in the region defined by the hollow body and the template.

8 Claims, 6 Drawing Sheets

BONE MILLING GUIDE APPARATUS AND METHOD

BACKGROUND

1. Field of the Invention

This invention relates to hip stem prothesis apparatus and, more particularly, to a novel bone milling guide apparatus and method for the precision milling of a socket into the medullary cavity of the proximal femur of a patient, the socket thereby being prepared to receive a hip stem in a close-fitting relationship.

2. The Prior Art

Total hip replacement is one of the most remarkable advances in orthopedic surgery of this century. Since the first total hip joint replacement in 1962, significant advances have been made in both implant design and surgical technique. These improved devices and procedures offer new hope for patients crippled by degenerative arthritis, rheumatoid arthritis, or significant trauma to the hip. Diseases such as rheumatoid or osteo-arthritis generally result in degradation of the cartilage lining the acetabulum so that the ball of the femur rubs against the ilium. This rubbing action causes pain and further degradation of the remaining cartilage. Bone erosion causes the affected bones to attempt to compensate by reshaping, thus resulting in a misshapen joint which may eventually cease to function altogether.

Total joint replacement can provide not only marked resolution of pain but significant functional improvement. Currently, approximately 250,000 successful total joint replacements are performed each year in the United States alone so that the replacement of a hip joint with an artificial implant or prosthetic device is now a routinely practiced surgical procedure. The long-term success rate following total hip replacement is excellent. It is estimated that over 90% of patients who have had total joint replacement are functioning well 12 years after surgery.

A conventional hip prosthesis consists of an artificial femur head or ball mounted on the neck end of a stem with the ball being received in a prosthetic acetabular socket affixed to the ilium. The proximal end of the femur is removed and the stem is anchored in the medullary bone cavity. Despite overall excellent results, problems may infrequently develop following total joint replacement. The major potential complication of total joint replacement is infection. Pain following total joint replacement may also be due to mechanical loosening or breakage of the implant resulting in excessive motion between the prosthesis and the underlying bone. In relatively rare instances, a second, total joint replacement or revision may be required. It is estimated that approximately five percent of all total joint replacements performed today are revisions of previous procedures.

One of the major problems encountered during joint-replacement surgery is the need to securely anchor the hip stem portion of the prosthesis in the medullary bone cavity. Numerous attempts have been made to solve this particularly vexing problem. Early procedures involved reaming most of the cancellous bone from the proximal end of the medullary canal followed by packing the resulting cavity surrounding the prosthetic hip stem with bone cement so as to assure fixation between the hip stem and the surrounding cortical bone. Bone cement was necessitated because the metaphyseal geometry does not necessarily have any relationship to diaphyseal geometry, and it was found to be virtually impossible to predetermine the precise configuration for the prosthetic device. Accordingly, the customary practice was to use the cement material to achieve fixation by using it as a filler between the hip stem and the adjacent cortical bone. Unfortunately, revision is also rendered considerably more difficult by the presence of bone cement.

Clinical experience by a noted orthopedic surgeon over the last decade has demonstrated that, in the short term, cemented arthroplasties are more forgiving than those designed for biologic fixation. For example, it was found that it was rare for a patient with a cemented arthroplasty to experience clinical symptoms of fixation failure within the first few postoperative years. In contrast, a technically poor insertion of a porous-coated implant often results in fixation failure from the very start, with patient dissatisfaction as soon as weight bearing is allowed.

A more suitable alternative that has evolved is that of a noncemented total hip replacement wherein the prosthesis is implanted in the absence of a cement. The potential for adequate bone ingrowth to create an enduring cementless implant fixation can be realized only if stable fixation is achieved from the start, particularly since fixation through bone ingrowth succeeds or fails within the first several months after implantation. The most important prerequisite for secure fixation and better physiological stress transfer between implant and osseous tissue is initial mechanical stability. Micromotion between the implant and the surrounding osseous tissue into which it is inserted must be minimal during the time when the intramedullary fracture callus adjacent the implant is differentiating into osseous tissue and maturing. This initial mechanical stability can only be achieved with careful preoperative planning, meticulous surgical technique and a wide selection of incrementally sized hip stem components.

The fundamental problem is still that of the range of anatomical variations encountered in the femur. Basically, the medullary cavity of the femur is in the shape of an inverted, triangular pyramid at the top and a rod at the bottom. The first problem during preparation of the medullary cavity is to match the diaphysis which can be done by simple reaming to define the size of the stem. The second problem is to match the proximal end of the stem to the cortical bone. One approach is to provide the stem with a size range of sleeves which can be mounted to the stem in a locking relationship using a conventional Morse taper. Not only does the Morse taper allow one to use a preselected sleeve size, but it also accommodates placement of the triangular portion of the sleeve at a preselected angle to the neck of the stem.

From the foregoing it can be readily seen that the preparation of the proximal end of the femur to receive the proximal end of the hip stem is the major challenge. One bone milling device is disclosed by Frey et al (U.S. Pat. No. 4,777,942) and includes a milling instrument having a caliper that is inserted into the medullary cavity. A spindle is linked to the caliper at an angle and carries a milling cutter as well as a guide shoe at its distal end. The guide shoe slides within a guideway on the distal end of the caliper. The instrument guides the milling cutter to cut a circular arc corresponding to the boundary line between the spongiosa and cortical tissue in the region of the calcar arc.

Forte (U.S. Pat. No. 4,306,550) discloses a combination of tools and methods used to prepare a socket in a femur for receiving a femoral prosthesis. A rasp is used to form a socket in the femur. A cutter is journaled to the rasp prior to its removal and is rotated to machine the surface of the calcar surrounding the socket.

Experience has shown that these prior art devices are complex and require extensive experience before they can be used with any suitable degree of accuracy. Further, even experienced surgeons must rely heavily on personal expertise to accommodate for the fact that neither of these prior art devices accurately control the preparation of the medullary cavity or socket with a suitable degree of precision.

In view of the foregoing it would be an advancement in the art to provide a bone milling guide to enable the surgeon to easily and accurately mill the proximal end of a femur to receive a hip stem prosthesis. It would also be an advancement in the art to provide a bone milling guide that is simple to use and is mountable in the socket prepared to receive the distal stem of the prosthesis. Such a novel apparatus and method is disclosed and claimed herein.

BRIEF SUMMARY AND OBJECTS OF THE INVENTION

This invention is a bone milling template that is used to enable the surgeon to accurately and easily guide a bone miller in the preparation of the intramedullary cavity in the proximal end of the femur to receive the proximal end of a hip stem in close-fitting relationship. The template is demountably attached to a probe that is inserted into the bore created to receive the distal stem. The template accurately controls the movement of the bone miller in cutting a socket to receive the proximal end of the hip stem.

It is, therefore, a primary object of this invention to provide improvements in cutting control devices for controlling the cutting of bone to receive a hip stem.

Another object of this invention is to provide improvements in the method of preparing the proximal end of a femur to receive a hip stem.

Another object of this invention is to provide a template apparatus for accurately guiding a bone miller in cutting the proximal end of a femur to receive a hip stem.

Another object of this invention is to provide a template for a calcar miller wherein the position of the template is fixed by being partially inserted into a truncated cavity created in the intramedullary canal.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
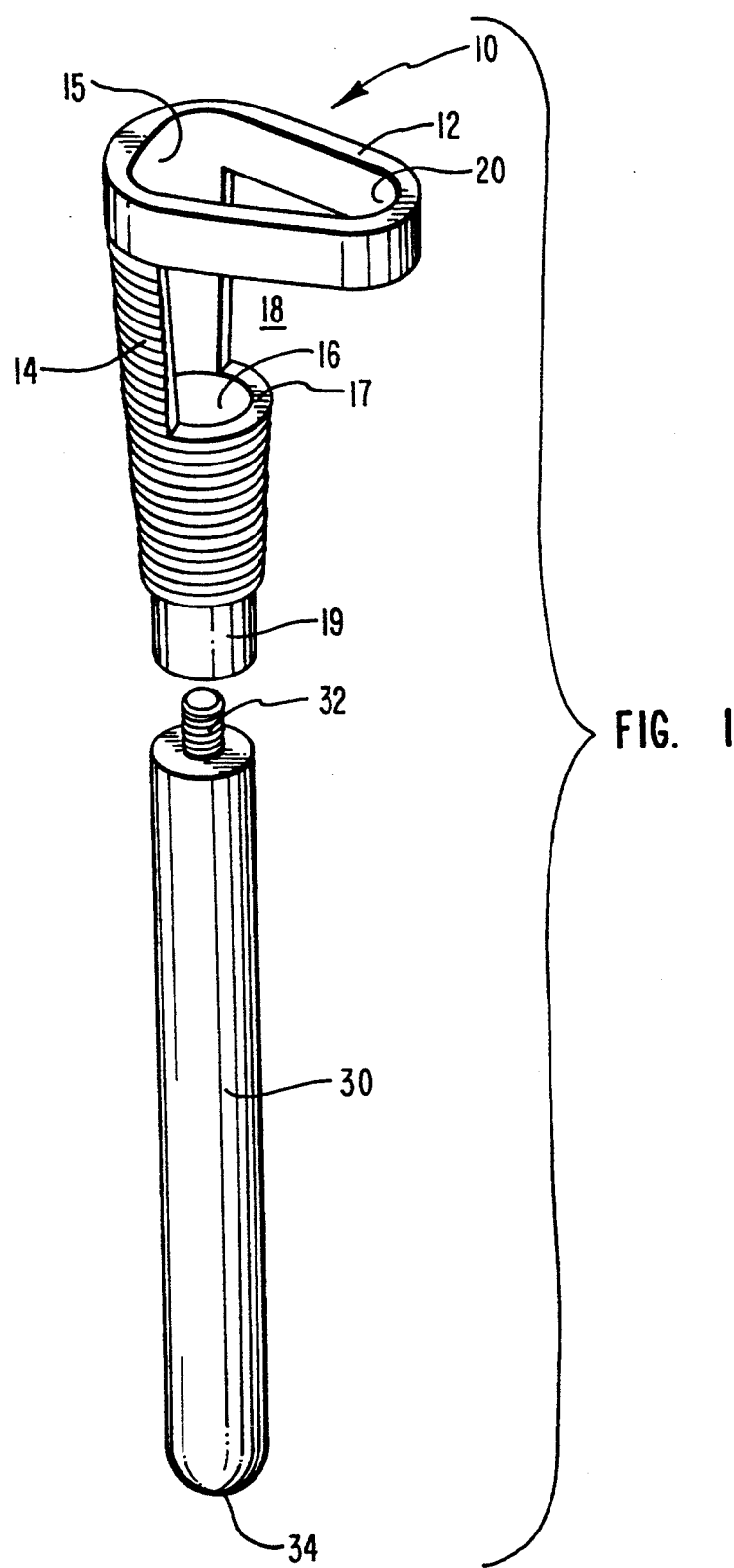
FIG. 1 is an exploded, perspective view of the novel bone milling guide of this invention shown in the presence of a distal stem guide.

The invention is best understood by the following description and appended claims with reference to the drawing wherein like parts are designated by like numerals throughout.

General Discussion

Bone consists of two basic types of tissue: hard or compact bone which is dense in texture, and soft or cancellous bone which consists of fibers and lamellae joined together to form a reticular network. The hard bone tissue is generally referred to as the cortical bone and constitutes the outer wall of the bone where it provides most of the overall strength of the bone. The thickness of the cortical bone varies at different positions along the length of the bone with the greatest thickness along the midpoint where the cross sectional area of the bone is the smallest. The cortical bone is thinner adjacent the ends where the bone flares outwardly to support the particular joint mechanism.

Where present, cancellous bone forms the inner core of the bone with the major portions of cancellous bone being found adjacent the ends of the bone where the cross sectional area is the greatest and, correspondingly, where the cortical bone is the thinnest. It is currently believed that the cancellous bone in these regions contributes to the overall strength of the bone by transferring a portion of the applied stresses from the thin sections of cortical bone to the relatively large areas of thicker cortical bone located closer to the midsection of the bone. In these regions of stress transfer, the fibers making up the cancellous bone appear to have a regular equipotential-like arrangement wherein fibers intersect the internal surface of the cortical bone at spaced intervals of approximately one to two millimeters. It is believed that this arrangement, at least in part, is responsible for the efficient transfer of applied stress from one part of the cortical bone to another.

The proper implantation of a prosthesis into an intramedullary cavity created in the cancellous bone involves very close tolerances in order to achieve good initial fit. Good initial fit is important because of its direct correlation to a smoother postoperative course involving less adaptive bone remodeling and earlier weight bearing. One study underscored the importance of a quality initial fit wherein it was found to be the most significant factor influencing outcome. Surprisingly, the quality of the initial fit was even more important than any of bone quality, diagnosis, age, and sex. These latter factors were found to be of lesser significance in predicting results. The goal of a good fit is to optimally fill the intertrochanteric area in the coronal plane. Clearly, a limited degree of compromise is required between the shape of the implant versus the intertrochanteric area by the simple fact of the wide variations found among femurs. The reasonable alternative, therefore, is to accurately shape the intramedullary cavity so as to receive the implant in a precision, scratch-fit relationship.

Detailed Description

Figure 2:
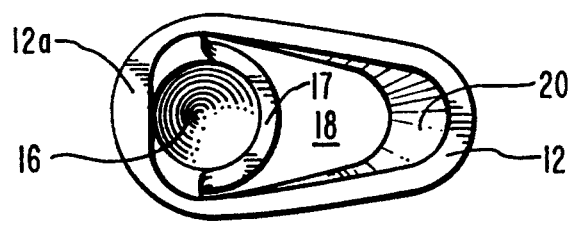
FIG. 2 is a plan view of the bone milling guide.
Figure 3:
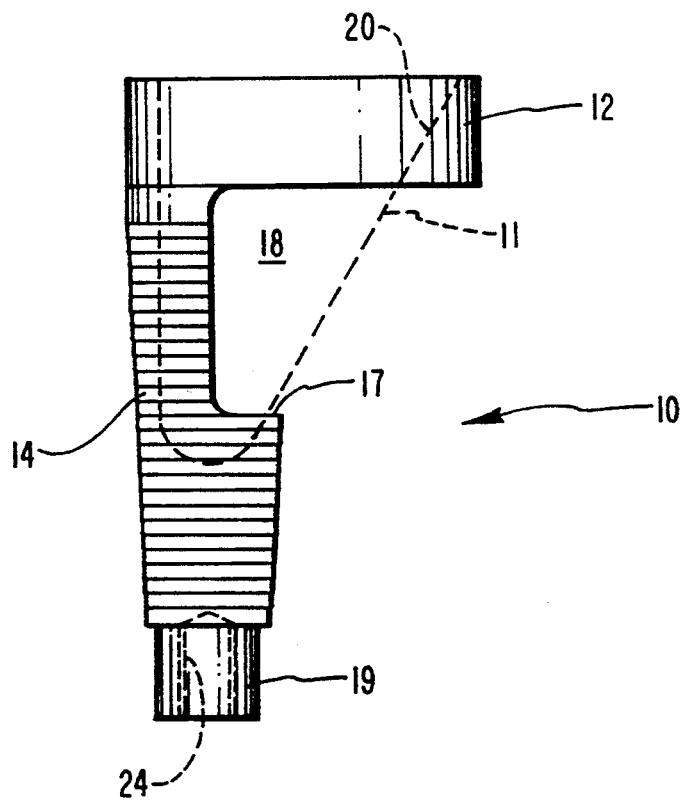
FIG. 3 is a side elevation of the bone milling guide.
Figure 6:
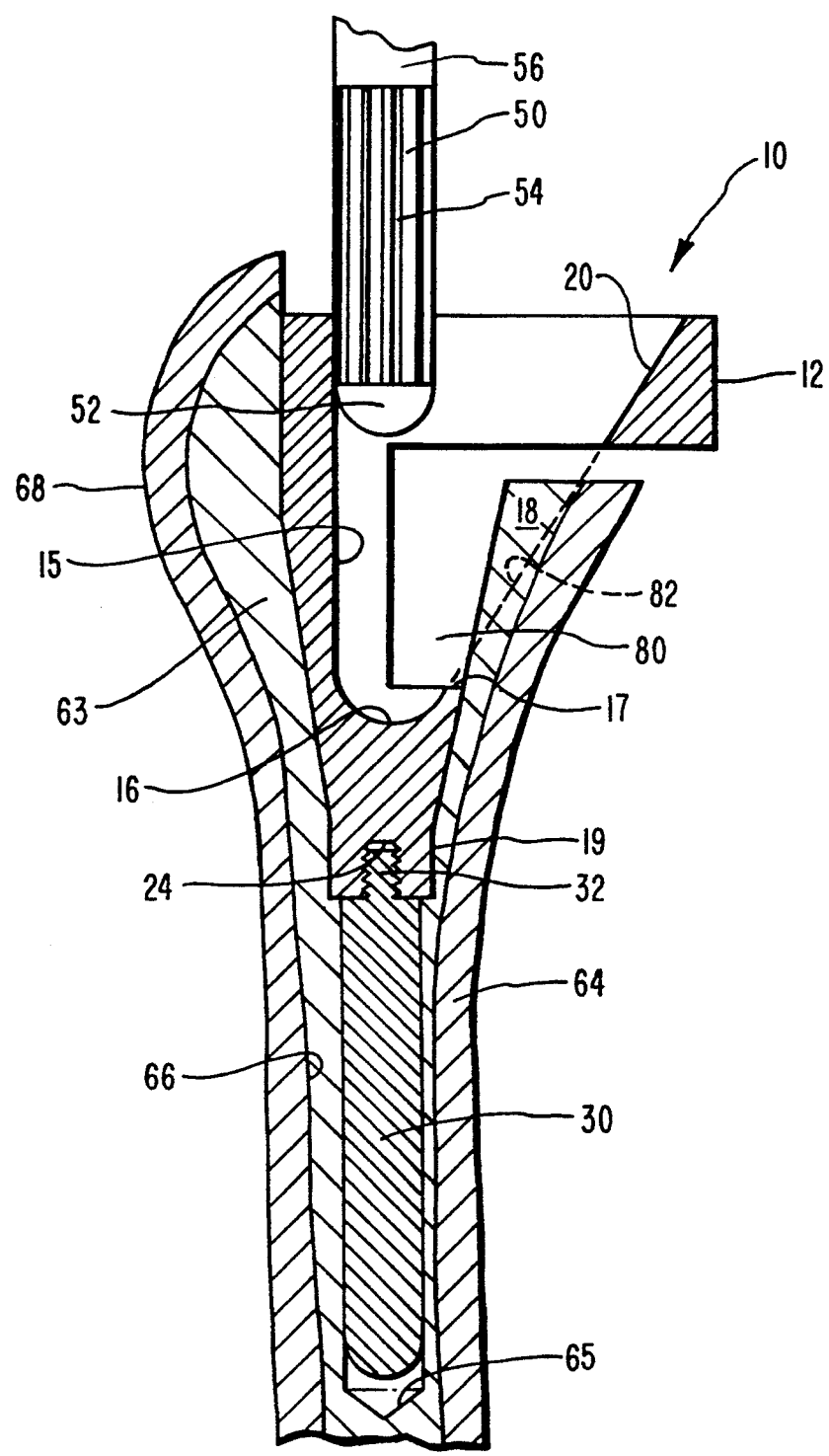
FIG. 6 is a cross sectional view of the proximal end of the femur of FIG. 5 with the bone milling guide in place in the medullary cavity and in the presence of a bone miller.
Figure 7:
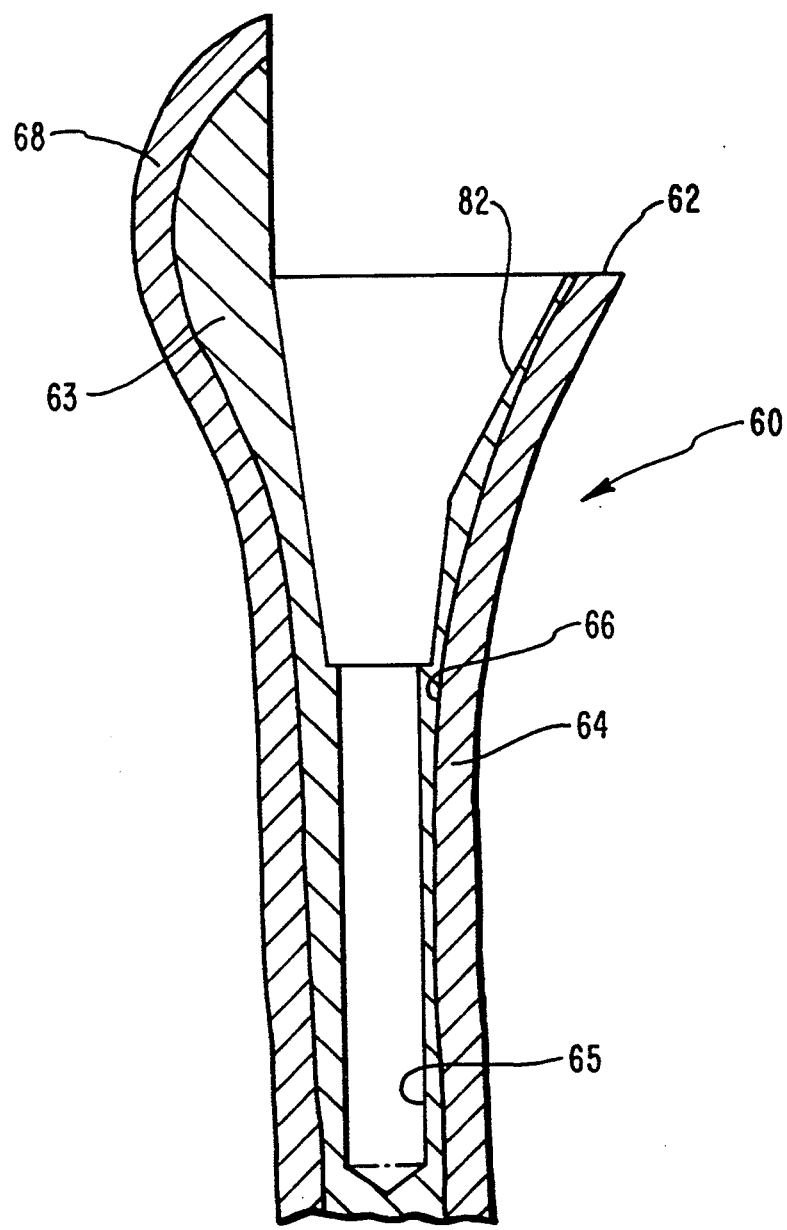
FIG. 7 is a cross sectional view of the proximal end of the femur of FIG. 6 showing the intramedullary cavity prepared through the use of the bone milling guide of this invention.

Referring now to FIGS. 1–3, the novel bone milling guide of this invention is shown generally at 10 and includes a template 12 extending from an upper edge of a hollow body 14. Hollow body 14 is configured with a vertical sidewall 13 formed with an external profile having a downwardly oriented taper as a portion of a truncated, right circular cone, the external profile of which closely approximate the shoulder region of the hip stem prosthesis (not shown) to be inserted in the intramedullary cavity 82 (FIG. 7). One side of hollow body 14 opposite vertical sidewall 13 is open as an opening 18 to expose the adjacent cancellous bone 63 (FIG. 6) to bone miller 50 (FIG. 6) as will be described more fully hereinafter. Interiorly, hollow body 14 has a coaxial cavity 15 configured as a downwardly tapered cavity terminating in a socket 16. The basal end of hollow body 14 terminates in a short, cylindrical base 19 which serves as a mounting surface for a guide 30 releasably mounted to hollow body 14.

Template 12 extends outwardly from one side of the upper edge of hollow body 14 and is configured with a generally tapered, lozenge shape as shown in the plan view of FIG. 2. Template 12 includes an inwardly sloped inner face 20, the slope of which corresponds to an imaginary line 11 (FIG. 3) extending between inner face 20 and a rim 17 forming a face of socket 16 located coaxially in the base of hollow body 14. Template 12 extends outwardly and orthogonally to the axis of hollow body 14.

The inner face of template 12 is provided with an inwardly-sloped surface 20, the slope of which corresponds to an imaginary surface extending upwardly from a rim 17 of socket 16. The region defined by the imaginary surface extending between sloped surface 20 and rim 17 is designated by cutout region 18. Cutout region 18 represents the portion of cancellous bone 63 (FIGS. 4–6) to be removed by a bone miller 50 (FIG. 5) as will be discussed more fully hereinafter.

Guide 30 has a threaded, coaxial boss 32 at a proximal end and is configured to be threadedly engaged to hollow body 14 at base 19 and includes a rounded tip 34 at a distal end. Guide 30 is adapted to be releasably mounted to base 19 in a coaxial relationship with hollow body 14 by threaded boss 32 being threadedly engaged in a corresponding threaded bore 24. Guide 30 is configured to be inserted into a hole 65 (FIGS. 4–6) drilled into the intramedullary canal 66 of bone 60. Guide 30 has a smooth, cylindrical profile and is designed to slidingly engage the cancellous bone 63 forming the sidewall of bore 65 drilled therein.

Figure 4:
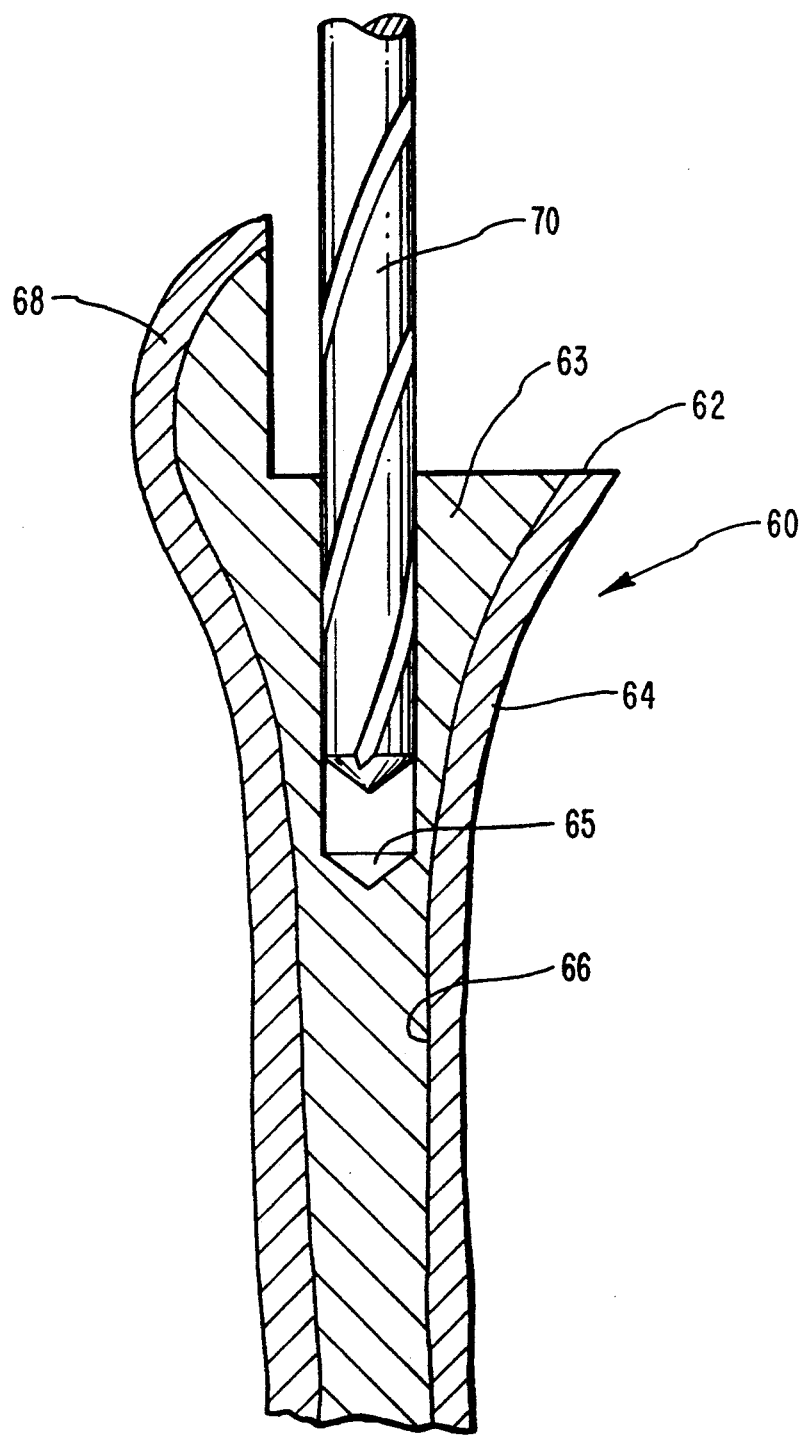
FIG. 4 is a cross sectional view of a proximal end of a femur shown in the process being drilled to receive a distal stem.

Referring now to FIG. 4, a bone 60 is shown schematically and in a cross sectional view with the ball portion (not shown) removed leaving a major portion of the greater trochanter 68 intact. The calcar region 62 is shown cut horizontally across the end of bone 60 which includes both cortical bone 64 and cancellous bone 63. Hole 65 is drilled into intramedullary canal 66 according to conventional techniques using a drill 70. The diameter and length of drill 70 are selected by the surgeon (not shown) so as to provide the appropriate size of hole 65 to receive the guide 30 (FIGS. 1 and 6) and pilot 74 (FIG. 5) prior to insertion of the distal stem of a hip stem prosthesis (not shown).

Figure 5:
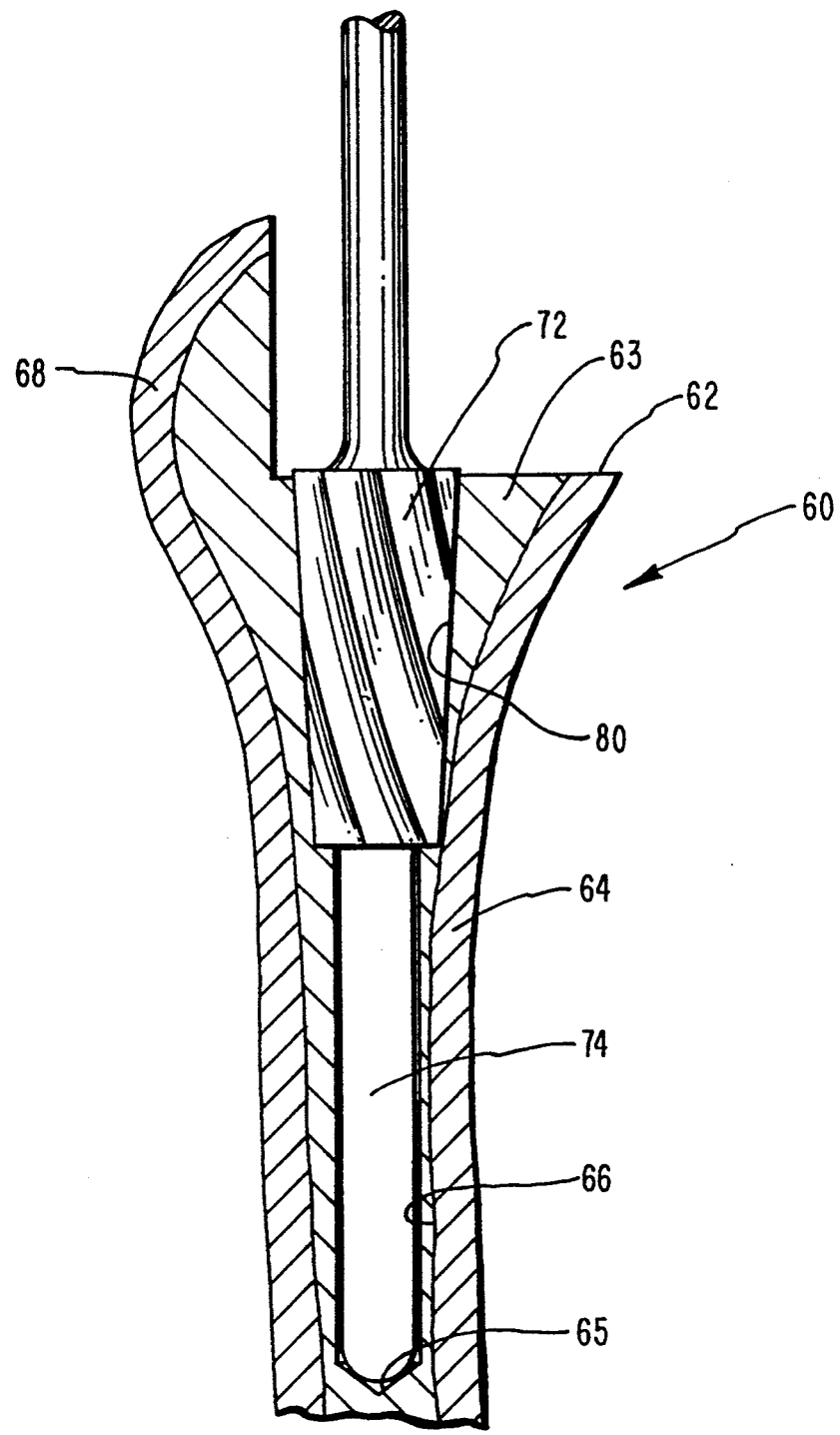
FIG. 5 is a cross sectional view of the proximal end of the femur of FIG. 4 being reamed at its proximal end to receive the truncated portion of the bone milling guide.

Referring now to FIG. 5, hole 65 is shown as having been completed in cancellous bone 63 and a reamer 72 has been used to cut into cancellous bone 63 to prepare a cavity 80 in the same for insertion of bone milling guide 10 (FIGS. 1–3 and 6) as will be discussed in reference to FIG. 6. Reamer 72 is a conventional reamer having a frustoconical profile and is adapted to have a distal pilot 74 releasably affixed thereto. The external profile of reamer 72 is configured to conform to the external profile of hollow body 14 (FIGS. 1–3 and 6). Distal pilot 74 is inserted into hole 65 so as to control reamer 72 in reaming the frustoconical portion of cancellous bone 63. Distal pilot 74 is essentially identical to guide 30.

Referring now to FIG. 6, bone milling guide 10 has been inserted into a cavity 80 created by reamer 72 (FIG. 5) in cancellous bone 63. Bone milling guide 10 is directed into cavity 80 by guide 30 being releasably secured to bone milling guide 10 and inserted into hole 65. Template 12 is held an incremental distance above the cortical bone 64 surrounding calcar region 62. Thus secured, bone milling guide 10 is now ready to receive therein bone miller 50. Bone miller 50 has a rounded tip 52, a milling surface 54, and an upper, guide follower 56.

The cutout region 18 shown in FIG. 1 is now seen as a segment of cancellous bone 63 residing between cavity 80 and a dashed line 11 extending between rim 17 and sloped surface 20 on template 12. Cutout region 18 represents the segment of cancellous bone 63 to be removed by a bone miller 50. Bone miller 50 is inserted downwardly into bone milling guide 10 along the axis of cavity 15 until rounded tip 52 is received in socket 16. Bone miller 50 is then moved in an arcuate path with guide follower 56 following the profile defined by sloped surface 20 of template 12 while rounded tip 52 is held in socket 16. The movement of bone miller 50 in this arcuate path allows milling surface 54 to remove all of cancellous bone 63 in cutout region 18 providing cavity 80 with an enlarged cavity 82 as defined by dashed line 19 and also as shown in FIG. 7.

Referring now to FIG. 7, bone milling guide 10 and guide 30 have been removed from bone 60 leaving a precision machined cavity 82, which in combination with hole 65, is prepared to accurately receive the preselected hip stem (not shown) in snug-fitting relationship. Advantageously, hole 65 and cavity 82 are prepared quickly and accurately in comparison with the prior art techniques and, more importantly, with a far superior degree of precision.

The Method

Referring now to all of FIGS. 1–7, the procedure for using bone milling guide 10 is described. Once bone 60 has been surgically exposed, the ball portion thereof (not shown) is removed according to conventional surgical techniques leaving intact as much of the greater trochanter 68 as possible. Importantly, the calcar surface 62 is prepared so as to receive thereon, the abutment surface of the hip stem prosthesis (not shown). Drill 70 is directed along the axis of the intramedullary canal 66 leaving hole 65 therein. Advantageously, drill 70 removes the cancellous bone 63 to preclude fragments thereof from becoming compacted in the bottom of hole 65.

Guide 74 is mounted on the basal end of reamer 72 and directed into hole 65. The diameter of guide 74 is incrementally smaller than the diameter of hole 65 so as to allow hole 65 to telescopically receive guide 74 in rotational relationship therewith. Guide 74 is used to directionally control the downward traverse of reamer 72 into cancellous bone 63 thereby providing an accurately machined, frustoconical cavity 80 in cancellous bone 63. The cancellous bone machined from cavity 80 is also removed by reamer 72 and not allowed to become compacted in the bottom of hole 65.

Hollow body 14 of bone milling guide 10 is dimensionally configured to be received in cavity 80 in snug-fitting relationship. Prior to inserting bone milling guide 10 into cavity 80, guide 30 is mounted thereto to provide alignment of bone milling guide 10 relative to bone 60. Template 12 is held an incremental distance above calcar surface 62 and the orientation of bone milling guide 10 relative to bone 60 is adjusted according to the surgical technique employed.

Bone miller 50 is then directed coaxially into hollow body 14 until rounded tip 52 is received in socket 16. Guide surface 56 is brought into contact with sloped surface 20 along the inner face of template 12 to thereby cause bone miller 50 to remove the underlying portion of cancellous bone 63 to enlarge a side portion of cavity 80 into cavity 82. The resulting cavity 82 has thereby been machined with precision. The resulting fragments (not shown) of cancellous bone 63 are removed to prevent them from becoming compacted in hole 65. With the completion of cavity 82, bone milling guide 10 along with distal guide 30 are removed from bone 60. Any residual fragments of cancellous bone 63 are also removed from cavity 82 and hole 65 prior to the insertion of the hip stem prosthesis (not shown). Importantly, the novel bone milling guide 10 apparatus and method of this invention readily enables the surgeon (not shown) to accurately and relatively quickly prepare cavity 82 to receive the appropriate hip stem prosthesis (not shown) in snug-fitting relationship. Further, this snug-fitting relationship is achieved in the absence of fragments of cancellous bone 63 becoming compacted in hole 65 as is the case when conventional reaming techniques are employed. Advantageously, the sizes of drill 70, reamer 72, and the contour of the cut defined by template 12 through the use of bone miller 50 are all selectively predetermined and coordinated with corresponding elements of the hip stem prosthesis (not shown) to provide an accurately machined cavity 82 for receiving therein the hip stem prosthesis (not shown) in a snug, close-fitting relationship. Such a fit assures a more secure ingrowth of bone earlier and also a much earlier weightbearing capability.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for guiding a bone miller for preparing the proximal end of a femur to receive a hip stem in snug-fitting relationship in said proximal end comprising:

drilling an axial bore in the intramedullary canal of said femur;

forming a tapered recess at the proximal end of said axial bore;

mounting a guide axially to a distal end of a tapered hollow body;

shading a template for the upper end of said hollow body, said template having a noncircular profile in a closed loop and extending orthogonally from said upper end;

removing a portion of the sidewall of said hollow body below said template thereby providing an open side for said hollow body;

inserting said tapered, hollow body into said tapered recess while directing said guide into said axial bore, said guide assisting in supporting said hollow body in said tapered recess;

directing a bone miller into said hollow body; and guiding the bone miller outwardly with said template thereby cutting bone exposed by said open side while limiting outward travel of the bone miller with said template.

2. The method defined in claim 1 wherein said inserting step includes elevating a portion of said template above said proximal end of said femur to permit visual observation of said proximal end during said milling step.

3. The method defined in claim 1 wherein said directing step includes selecting said bone miller with preselected dimensions so as to be fittingly received into said hollow body and said template.

4. A bone milling guide for directing a bone miller while producing a cavity in the intramedullary canal in the proximal end of a femur, the cavity being prepared to receive the proximal end of a hip stem in a snug fitting relationship, the intramedullary canal having been previously drilled to produce a bore in the intramedullary canal, the cavity being prepared as an enlargement of the bore and with a noncircular profile when viewed in cross section, said bone milling guide comprising:

a basal element configured to be received in the bore;

a socket in the upper surface of said basal element, said socket having a raised rim and being dimensionally configured to receive a rounded ball on the end of the bone miller;

a vertical sidewall extending upwardly from a segment of said rim of said socket, said vertical sidewall having an external profile corresponding to a segment of the bore, said vertical sidewall extending from said basal element to an elevated position extending incrementally above the upper surface of the femur so that said vertical sidewall extends out of the bore to an upper end of said vertical sidewall; and a noncircular, closed loop mounted to said upper end of said vertical sidewall and residing in a plane oriented laterally above the proximal end of the femur, said noncircular, closed loop forming a template for guiding the upper end of the bone miller while the rounded ball of the bone miller is engaged in said socket.

5. The bone milling guide defined in claim 4 wherein said basal element is configured with a frustoconical profile when the bore is prepared with a frustoconical profile, the dimensions of said basal element being selectively predetermined to enable said basal element to be telescopically received in the bore.

6. The bone milling guide defined in claim 4 wherein said vertical sidewall comprises a curved surface extending between said basal element and said noncircular, closed loop, the external contour of said vertical sidewall corresponding to the contour of the bore.

7. The bone milling guide defined in claim 6 wherein said vertical sidewall comprises an arcuate surface that conforms to a portion of the arc of the bore, the internal wall of said arcuate surface receiving the bone miller inserted into the bore into contact with said socket.

8. The bone milling guide defined in claim 6 wherein said basal element includes a guide removably mounted to said basal element, said guide being received into a bore extension extending downwardly into the bone from the bore.

* * * * *